United States Patent
Roberge et al.

(10) Patent No.: US 10,300,055 B2
(45) Date of Patent: May 28, 2019

(54) TREATMENT OF PARKINSON'S DISEASE THROUGH ARFGAP1 INHIBITION

(71) Applicant: Dalhousie University, Halifax, Nova Scotia (CA)

(72) Inventors: Michel Roberge, Halifax (CA); Chris McMaster, Halifax (CA); Carla Zimmerman, Halifax (CA); Pak Poon, Halifax (CA)

(73) Assignee: DALHOUSIE UNIVERSITY, Halifax, Nova Scotia (CA)

( * ) Notice: Subject to any disclaimer, the term of this patent is extended or adjusted under 35 U.S.C. 154(b) by 89 days.

(21) Appl. No.: 15/302,930

(22) PCT Filed: Apr. 10, 2015

(86) PCT No.: PCT/CA2015/050295
§ 371 (c)(1),
(2) Date: Oct. 7, 2016

(87) PCT Pub. No.: WO2015/154191
PCT Pub. Date: Oct. 15, 2015

(65) Prior Publication Data
US 2017/0020866 A1    Jan. 26, 2017

Related U.S. Application Data

(60) Provisional application No. 61/978,091, filed on Apr. 10, 2014.

(51) Int. Cl.
| | | |
|---|---|---|
| *A61K 31/381* | (2006.01) | |
| *A61K 31/495* | (2006.01) | |
| *A61K 31/4402* | (2006.01) | |
| *C07D 213/61* | (2006.01) | |
| *C07D 213/74* | (2006.01) | |
| *C07D 295/073* | (2006.01) | |
| *A61K 31/496* | (2006.01) | |
| *A61K 31/4425* | (2006.01) | |

(52) U.S. Cl.
CPC .......... *A61K 31/495* (2013.01); *A61K 31/381* (2013.01); *A61K 31/4402* (2013.01); *A61K 31/4425* (2013.01); *A61K 31/496* (2013.01); *C07D 213/61* (2013.01); *C07D 213/74* (2013.01); *C07D 295/073* (2013.01)

(58) Field of Classification Search
None
See application file for complete search history.

(56) References Cited

FOREIGN PATENT DOCUMENTS

| | | |
|---|---|---|
| CA | 2540186 | 7/2005 |
| CA | 2568524 | 12/2005 |
| CA | 2652449 | 11/2007 |
| CA | 2687790 | 12/2008 |
| CA | 2690299 | 12/2008 |
| CA | 2725445 | 12/2009 |
| CA | 2809557 | 3/2012 |
| CA | 2827648 | 11/2012 |
| JP | 10-502670 A | 3/1998 |
| JP | 2013-537218 A | 9/2013 |
| WO | 97/28128 | 8/1997 |
| WO | 2012/162254 A1 | 11/2012 |
| WO | 2013/033037 | 3/2013 |

OTHER PUBLICATIONS

Hong et al., Front. Mol. Neurosci., 2014, vol. 7, article 52, pp. 1-10.*
ChemBridge 5468123, https://www.hit2lead.com/screening-compounds/5468123, accessed Sep. 26, 2017.*
PCT Search Report and Written Opinion dated Jul. 9, 2015 in PCT/CA2015/050295, filed Apr. 10, 2015, Applicant Dalhousie University, 18 pages.
Lee, B. D. et al.: "Inhibitors of leucine-rich repeat kinase-2 protect against models of Parkinson's disease", Nature Medicine, vol. 16, 2010, pp. 998-1000.
Feenstra, R. et al.: "SLV308", Drugs of the Future, vol. 26(2), 2001, pp. 128-132.
Duncan, M. C. et al.: "Composite synthetic lethal identification of membrane traffic inhibitors", PNAS, vol. 104(15), 2007 pp. 6235-6240.
Li, Z. et al.: "Discovery and Preliminary Structure-Activity Relationship of Arylpiperazines as Novel, Brain-Penctrant Antiprion Compounds", Medicinal Chemistry Letters, vol. 4, 2013, pp. 397-401.
Faul, M. M. et al.: "Green Chemistry Approach to the Synthesis of N-Substituted Piperidones", JOC, vol. 68, 2003, pp. 5739-5741.
CAS : 915879-01-5.
CAS : 296792-87-5.
Banner, C. T. et al.: "Quternary Salts of Halogenated Pyridines and Quinolines", JACS, vol. 73, 1951, pp. 3499-3501.
E. Greggio and M.R. Cookson, "Leucine-rich repeat kinase 2 mutations and Parkinson's disease: three questions," ASN Neuro, vol. 1, No. 1, pp. 13-24, 19 (2009).
K. Stafa et al., "GTPase activity and neuronal toxicity of Parkinson's Disease-associated LRRK2 is regulated by ArfGAP1," PLoS Genetics, vol. 8, No. 2, e1002526, pp. 1-25 (2012).

(Continued)

*Primary Examiner* — Jeffrey S Lundgren
*Assistant Examiner* — Stephanie K Springer
(74) *Attorney, Agent, or Firm* — Polsinelli PC; Brian McKnight; Ron Galant

(57) ABSTRACT

Methods are provided for the treatment of Parkinson's disease (PD) in patients bearing mutations in the LRRK2 gene. A therapeutically effective amount of piperazine derivative compounds are employed to inhibit the biological activity of ArfGAP1, inhibition that counteracts the deleterious effects of mutations in, or increased expression of, the LRRK2 protein.

6 Claims, 6 Drawing Sheets

(56) References Cited

OTHER PUBLICATIONS

Y. Xiong et al., "GTPase activity plays a key role in the pathobiology of LRRK2, PLoS Genetics," vol. 6, No. 4, e1000902, pp. 1-18 (2010).
Z. Liu et al., "A Drosophila Model for LRRK2-linked parkinsonism," PNAS, vol. 105, No. 7, pp. 2693-2698 (2008).
R.J. West et al., "Neurophysiology of Drosophila Models of Parkinson's Disease," Parkinson's Disease, Hindawi Publishing, vol. 2015, Article ID 381281, pp. 1-11 (2015).

* cited by examiner

TREATMENT OF PARKINSON'S DISEASE THROUGH ARFGAP1 INHIBITION

CROSS-REFERENCE TO RELATED APPLICATIONS

This application claims the benefit of Provisional Application Ser. No. 61/978,091 filed Apr. 10, 2014, titled, TREATMENT OF PARKINSON'S DISEASE THROUGH ARFGAP1 INHIBITION, which is herein incorporated by reference in its entirety.

FIELD OF THE TECHNOLOGY

This technology relates generally to methods for treating Parkinson's Disease, and more specifically, treating Parkinson's Disease through ARFGAP1 inhibition.

BACKGROUND

With more people living longer, there is an increasing prevalence of age-related neurodegenerative diseases such as Parkinson's disease (PD), with its progressive loss of mobility and cognitive function. Parkinson's disease results from death of dopaminergic neurons in the substantia nigra, resulting in the progressive impairment of motor function for afflicted patients. Earlier symptoms of the disease are movement-related, with characteristic signs of shaking, rigidity, and difficulty in initiating movements. Later symptoms of the disease include dementia. The often protracted nature of the decline in quality of life as a result of PD affects not only the individual suffering from PD, but also family members, health-care professionals and the health-care system that provide care for PD patients. Treatments directed toward the underlying and progressive pathophysiology of PD are limited.

SUMMARY

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Although many cases of parkinsonism are idiopathic, several genetic loci have been found to influence the development of PD, with some mutations implicated as risk factors for sporadic disease. Ten years ago, an autosomal dominant mutation in the LRRK2 gene was found to be causative for late-onset PD. Mutations in this gene were found to account for 4% of genetic and 1% of sporadic cases of PD. The LRRK2 gene product is part of a two-member protein kinase family, with the other family member (LRRK1) having no effect on PD pathogenesis (Civiero and Bubacco, 2012). LRRK2 is a multi-functional, multi-domain protein with both protein kinase and intrinsic GTPase activity (FIG. 1) (Kumar and Cookson, 2012). It is the kinase activity of LRKK2, enhanced and/or improperly regulated as suggested by the effects of the LRRK2 mutations that is thought to contribute to PD. In addition, LRRK2 may serve as a scaffold for intracellular signalling (Greggio, 2012). One target of LRRK2 kinase activity is LRRK2 itself, with autophosphorylation directed to the GTPase domain (Webber et al., 2011). Although there is a clear regulatory relationship between LRRK2 kinase function and LRRK2 GTPase activity, the details remain unclear.

In an attempt to identify regulators of LRRK2-mediated effects, studies have used a genetic approach with a model system, the yeast *Saccharomyces cerevisiae*. In those cells, the expression of full-length LRRK2 was found to have no effect on viability, in large part because full-length LRRK2 forms insoluble inclusion bodies (Xiong et al., 2010). However, expression of a truncated version of the LRRK2 protein did cause loss of yeast cell viability, and also affected intracellular vesicular trafficking in a manner dependent on the GTPase domain of LRRK2 (Xiong et al., 2010). In primary mouse neurons, expression of the same LRRK2 truncation caused the neurotoxicity, and similar trafficking problems as was observed in the *S. cerevisiae* cells, as did the over-expression of full-length LRRK2 (Xiong et al., 2010), leading researchers to conclude that use of a truncated protein in yeast cells provides a valid readout for the toxic effects of LRRK2 activity.

Through a whole-genome analysis approach, investigators found that deletion of several yeast genes minimizes the detrimental effects of the truncated LRRK2 protein (Xiong et al., 2010). One of the yeast genes whose deletion minimizes LRRK2 toxicity is the GCS1 gene, encoding a highly conserved GTPase-activating protein (GAP) that functions in vesicular transport (Poon et al., 1996). The mammalian ortholog of the yeast Gcs1 protein is ArfGAP1 (Cukierman et al., 1995). Tellingly, overexpression of human ArfGAP1 is toxic to yeast deleted of Gcs1 (FIG. 2). More recently, ArfGAP1 and LRRK2 were shown to interact in vitro, and in vivo in mouse brain (Stafa et al., 2012, Xiong et al., 2012). In vitro, the ArfGAP1 protein is a GAP for LRRK2 GTPase activity (FIG. 3). In turn, ArfGAP1 is a substrate for LRRK2-mediated phosphorylation (Stafa et al., 2012). More importantly, decreasing ArfGAP1 expression in primary neural cells mitigated some of the neurotoxic effects of mutant (PD-promoting) LRRK2 or of over-expression of normal LRRK2 (Stafa et al., 2012). These findings suggest that targeting ArfGAP1 with inhibitory drugs is an effective way to deal with the progression of LRKK2-related PD. To this extent, the identification of drugs that inhibit ArfGAP1 activity would serve as a significant therapeutic intervention for PD.

As mentioned previously, the budding yeast *Saccharomyces cerevisiae* can be used as an experimental system to identify small molecules that, through inhibition of these other proteins, can ameliorate the detrimental effects of altered LRRK2 activity. Significant insights into the molecular basis for many cellular processes including PD (Cooper et al., 2006; Gitler et al., 2008; Xiong et al., 2010, Stafa et al., 2012) and for the underlying basis of disease have come from the study of the yeast *Saccharomyces cerevisiae*. This budding yeast is widely studied, mainly due to the genetic and molecular facility that this system provides. Furthermore, the evolutionary conservation of core cellular processes allows findings within yeast to provide tremendous value in the human context. From yeast to mammalian cells there is structural and functional conservation of the components of many fundamental processes including vesicular trafficking (Baiter and Vogel, 2001; Bonifacino and Glick, 2004; Botstein et al., 1997). To this extent, an experimental screen of small molecules in yeast would reveal drugs beneficial in a human context based on this functional conservation.

Overall, the screening for ArfGAP1 inhibitors will lead to the identification of novel approaches for treatment of some forms of PD in which aberrant LRRK2 activity plays a role in disease progression. The present invention provides for a composition and method that safely and effectively treats individuals suffering from PD with LRRK2 mutations through the administration of therapeutically effective amounts of phenyl piperazine-derivative molecules.

In a further aspect, the invention provides for a composition and method that safely and effectively treats individuals suffering from generalized neurodegenerative conditions, including Alzheimer's disease, Huntington's disease, and Amyotrophic lateral sclerosis.

In a further aspect, the invention provides a kit comprising a pharmaceutical composition comprising phenyl piperazine-derivative small molecules, and instructions for administering to a subject the composition for treating a subject who is suffering from PD.

As used herein, the term "phenyl piperazine-derivative small molecule" is defined as any organic molecule that consists of a six-membered ring containing two nitrogen atoms at opposite positions in the ring with a phenyl group (C6H5) bonded to one of the nitrogens.

As used herein, a "nucleic acid" or a "nucleic acid molecule" means a chain of two or more nucleotides such as RNA (ribonucleic acid) and DNA (deoxyribonucleic acid).

As used herein, the term "inhibition" refers to the reduction of biological activity of a protein, preferably the reduction of activity of the human protein ArfGAP1.

As used herein, the term "gene" is meant a nucleic acid molecule that codes for a particular protein, or in certain cases, a functional or structural RNA molecule.

As used herein, "protein" and "polypeptide" are used synonymously to mean any peptide-linked chain of amino acids, regardless of length or post-translational modification, e.g., glycosylation or phosphorylation.

When referring to a nucleic acid molecule or polypeptide, the term "wild type" refers to a naturally-occurring (e.g., native, WT) nucleic acid or polypeptide.

As used herein, the terms "treatment" and "therapy" are defined as the application or administration of a therapeutic agent to a patient or subject, or application or administration of the therapeutic agent to an isolated tissue or cell line from a patient or subject, who has a disorder or disease, a symptom of disorder or disease or a predisposition toward a disorder or disease, with the purpose to cure, heal, alleviate, relieve, alter, remedy, ameliorate, improve or affect the disorder or disease, the symptoms of disorder or disease, or the predisposition toward disorder or disease.

The term "therapeutically effective amount", as used herein, means the amount of the piperazine-derivative small molecules that will elicit the desired therapeutic effect or response.

The terms "patient," "subject" and "individual" are used interchangeably herein, and mean a mammalian (e.g., human, rodent, non-human primates, canine, bovine, ovine, equine, feline, etc.) subject to be treated, diagnosed, and/or to obtain a biological sample from.

The term "kit" as used herein refers to a packaged product comprising components with which to administer the therapeutically effective amount of piperazine-derivative small molecule for treatment of PD. The kit preferably comprises a box or container that holds the components of the kit. The box or container is affixed with a label or a Food and Drug Administration approved protocol. The box or container holds components of the invention that are preferably contained within plastic, polyethylene, polypropylene, ethylene, or propylene vessels. The vessels can be capped-tubes or bottles. The kit can also include instructions for administering the piperazine-derivative small molecule.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof, which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
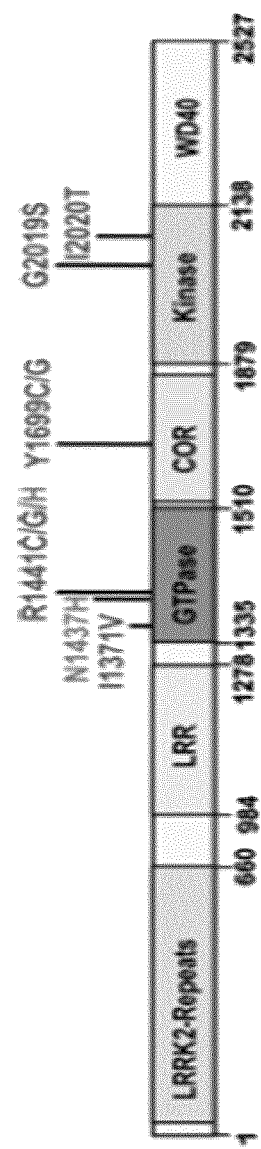
FIG. 1 illustrates the schematic domain structure of the LRRK2 protein. Residues 1-660 encode LRRK2-specific repeat sequences, residues 984-1278 encode the LRR domain, residues 1335-1510 encode the ROC GTPase domain, residues 1519-1795 encode the COR domain, residues 1879-2138 encode the kinase domain, and residues 2138-2527 encode the WD40 domain. The positions of mutations clearly segregating with disease are shown in red, whereas the positions of R1441H and N1437H associated with PD are highlighted in blue. The domain boundaries are indicated by the residue numbers in black.

Various embodiments of the disclosure are discussed in detail below. While specific implementations are discussed, it should be understood that this is done for illustration purposes only. All references cited within this disclosure are incorporated herein. A person skilled in the relevant art will recognize that other components and configurations may be used without parting from the spirit and scope of the disclosure.

Described are compositions and methods for treating Parkinson's disease through the administration of therapeutically effective amounts of substituted piperazine-derivative molecules. The treatment regime, in a preferred embodiment, is geared towards the treatment of LRRK2 mutation-induced PD through the inhibition of the ArfGAP1 protein.

In one embodiment, the therapeutically effective amount of the ArfGAP1 inhibitor has the general formula of

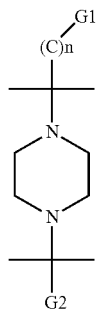

wherein n=0, 1 or 2; wherein G1 is (1) a unsaturated heterocyclic ring with five or six members, the unsaturated heterocyclic ring at least having a S or a N; or (2) a saturated carbocyclic ring with five or six members, the saturated carbocyclic ring at least being substituted with one or more of carboxylic acid or methanone, or being fused with benzene; or (3) a unsaturated bicycloheptene; or (4) a unsaturated methyl-substituted alkene with two to four Cs; and wherein G2 is (1) 4-acetophenone; or (2) 4-nitrobenzene; or (3) 2-pyridine. In a further embodiment, wherein n=1, G1 is 2-pyridine or 2-thiophene, and G2 is 4-acetophenone or 4-nitrobenzene.

In another embodiment, wherein n=1, G1 is methyl-substituted butene, and G2 is 4-nitrobenzene.

In another embodiment, wherein n=1, G1 is unsaturated bicycloheptene, and G2 is 4-nitrobenzene.

In another embodiment, wherein n=0, G1 is indane, and G2 is 2-pyridine.

In another embodiment, wherein n=0, G1 is formylcyclohexane carboxylic acid, and G2 is 4-nitrobenzene.

In another embodiment, the ArfGAP1 inhibitor for treating or preventing Parkinson's disease has the general formula of:

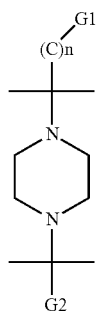

wherein n=0, 1 or 2; wherein G1 is (1) a unsaturated heterocyclic ring with five or six members, the unsaturated heterocyclic ring at least having a S or a N; or (2) a saturated carbocyclic ring with five or six members, the saturated carbocyclic ring at least being substituted with one or more of carboxylic acid or methanone, or being fused with benzene; or (3) a unsaturated bicycloheptene; or (4) a unsaturated methyl-substituted alkene with two to four Cs; and wherein G2 is (1) 4-acetophenone; or (2) 4-nitrobenzene; or (3) 2-pyridine.

In another embodiment, wherein n=1, G1 is 2-pyridine or 2-thiophene, and G2 is 4-acetophenone or 4-nitrobenzene.

In another embodiment, wherein n=1, G1 is methyl-substituted butene, and G2 is 4-nitrobenzene.

In another embodiment, wherein n=1, G1 is unsaturated bicycloheptene, and G2 is 4-nitrobenzene.

In another embodiment, wherein n=0, G1 is indane, and G2 is 2-pyridine.

In another embodiment, wherein n=0, G1 is formylcyclohexane carboxylic acid, and G2 is 4-nitrobenzene.

In another embodiment, the ArfGAP1 inhibitor for treating or preventing Parkinson's disease has the general formula of:

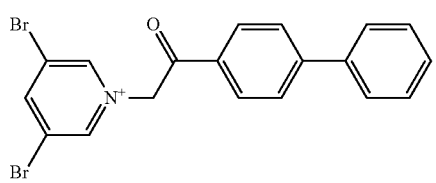

[2-(3,5-dibromo-1λ4-pyridin-1-yl)-1-(4-phenylphenyl)ethan-1-one]

Administration

Any suitable methods of administering a composition as described herein to a subject may be used. In these methods, the compositions can be administered to a subject by any suitable route, e.g., systemically by intravenous injection, directly to a target site, parenterally, orally, interathecally, interacranially, etc. The compositions may be administered directly to a target site by, for example, surgical delivery to an internal or external target site, or by catheter to a site accessible by a blood vessel. For example, in a method of treating PD, a composition as described herein may be delivered orally or intravenously. The compositions may be administered in a single bolus, multiple injections, or by continuous infusion (e.g., intravenously, or interathecally by peritoneal dialysis, pump infusion). For parenteral administration, the compositions are preferably formulated in a sterilized pyrogen-free form. As indicated above, the compositions described herein may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like. The compositions described herein may be administered to mammals (e.g., rodents, humans, nonhuman primates, canines, felines, ovines, bovines) in any suitable formulation according to conventional pharmaceutical practice (see, e.g., Remington: The Science and Practice of Pharmacy (20th ed.), ed. A. R. Gennaro, Lippincott Williams & Wilkins, (2000) and Encyclopedia of Pharmaceutical Technology, eds. J. Swarbrick and J. C. Boylan, Marcel Dekker, New York (1988-1999), a standard text in this field, and in USP/NF). A description of exemplary pharmaceutically acceptable carriers and diluents, as well as pharmaceutical formulations, can be found in Remington: supra. Other substances may be added to the compositions to stabilize and/or preserve the compositions.

The therapeutic methods described herein in general include administration of a therapeutically effective amount of the compositions described herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider. The methods and compositions herein may be used in the treatment of any other disorders or diseases relating to anemia.

Effective Doses

The compositions described herein are preferably administered to a mammal (e.g., human) in an effective amount, that is, an amount capable of producing a desirable result in a treated mammal (e.g., treating PD through administration of piperazine-derivative compounds). Such a therapeutically effective amount can be determined according to standard methods. Chemical analysis of isolated compounds, specifically piperazine-derived molecules have demonstrated a predicted ability to permeate through the blood-brain barrier for therapeutic purposes based on the following data concerning the compounds: MW: <400; Sum of (O+N): <5; PSA: <60-70 A; c Log P: <5.0; No of rotatable bonds <8; pKa: neutral or basic with pKa 7.5-10.5 (avoid acids); Non-Pgp substrate; Aqueous solubility: >60 ug/ml; Effective Permeability: >1×10$^{-6}$ cm/sec.

Toxicity and therapeutic efficacy of the compositions utilized in methods of the invention can be determined by standard pharmaceutical procedures. As is well known in the medical and veterinary arts, dosage for any one subject depends on many factors, including the subject's size, body surface area, age, the particular composition to be administered, time and route of administration, general health, and other drugs being administered concurrently. A delivery dose of a composition as described herein may be determined based on preclinical efficacy and safety.

EXAMPLES

The present invention is further illustrated by the following specific examples. The examples are provided for illustration only and should not be construed as limiting the scope of the invention in any way.

Screening of Small Molecules in Yeast

Overexpression of heterologous proteins in the yeast *Saccharomyces cerevisiae* often inhibits its growth, while inhibitors of the overexpressed proteins can restore growth. These simple observations form the basis of a powerful assay to identify inhibitors of such proteins. An expression plasmid for the inducible expression of a gene of interest is introduced into a yeast strain rendered more sensitive to chemicals by deletion of efflux pumps. Protein expression is induced, cells are exposed to test chemicals, and growth is measured by optical density at 600 nm (OD600 or A600) reading.

In the instant case, a *S. cerevisiae* gcs1 knockout strain is employed bearing a vector expressing the heterologous protein hArfGAP1 (human ArfGAP1, the human ortholog of yeast GCS1). Generally, expression of ArfGAP1 will suppress growth of gcs1 knockout yeast and thus small molecules that inhibit ArfGAP1 will lead to observable increases in growth. This in turn allows for the direct identification of small molecules that could be used to treat LRRK2-mutation induced PD.

Yeast Strains Employed in Inhibitor Screening

PPY17:114-3B-vec (gcs1::NatR, pdr5::HIS3, snq2::TRP1, ura3, ade2, carrying plasmid pRS315) [empty vector control strain]; PPY17:114-3B-141-A (gcs1::NatR, pdr5::HIS3, snq2::TRP1, ura3, ade2, carrying plasmid pPP16:141 pGAL1-hArfGAP1) [human ArfGAP1-expressing strain].

Generation of Synthetic Complex (SC) Mix, SC Dropout Mix, and SC Selection Medium Solutions Synthetic Complete (SC) mix: 0.6-g adenine, 0.6-g uracil, 0.6-g tryptophan, 0.6-g histidine, 0.6-g arginine, 0.6-g methionine, 0.9-g tyrosine, 0.9-g lysine, 1.5-g phenylalanine, 6.0-g threonine, 3.0-g aspartic acid, 1.8-g isoleucine, 4.5-g valine, 1.8-g leucine (Sigma). All ingredients are weighed, mixed together, and a mortar and pestle is used to grind the ingredients into a homogeneous powder. The powder is stored in 50-mL Falcon tubes at room temperature.

SC dropout mix: All the ingredients except for leucine are weighed, then mixed, ground, and stored as for the SC mix.

SC selection medium: Yeast nitrogen base without amino acid (BD/Difco, Sparks, Md.) 0.67% SC and dropout mix 0.067%, are dissolved in water. 0.25 mL of 1N NaOH is added to every 100-mL medium to raise the pH of the solution to 6.5. The solution is autoclaved and stored at room temperature.

Inhibitor Screening

Figure 2:
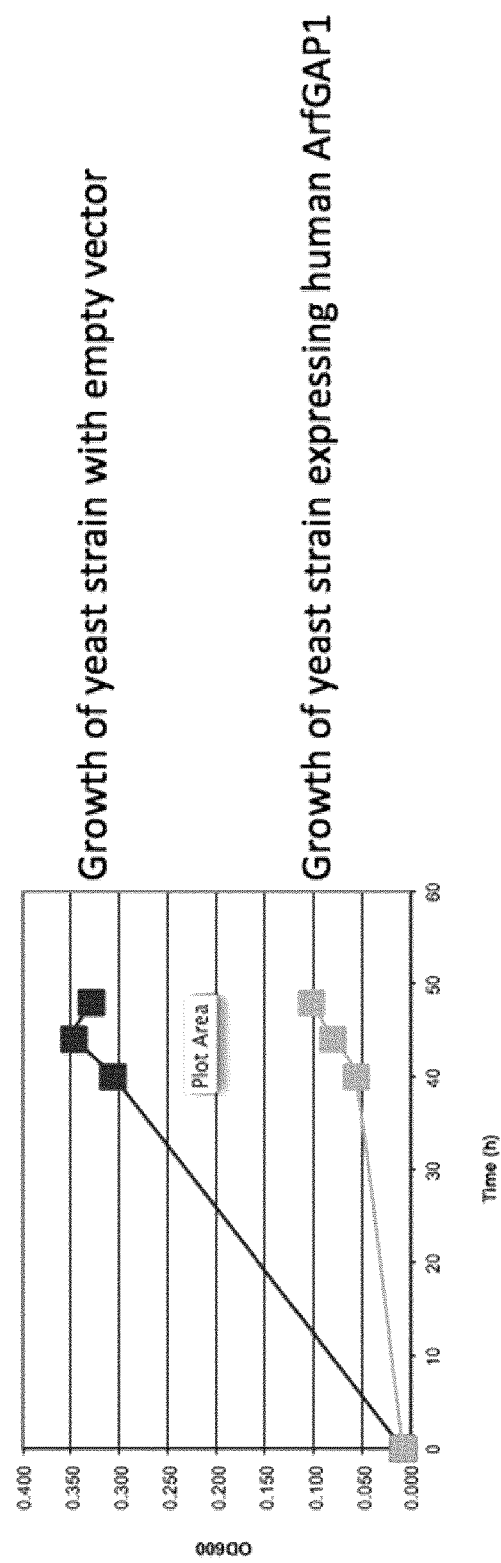
FIG. 2 illustrates experimental results in yeast cells, which demonstrate that expression of human ArfGAP1 causes a slow growth phenotype in yeast (bottom line) relative to yeast strains with empty vector.
Figure 3:
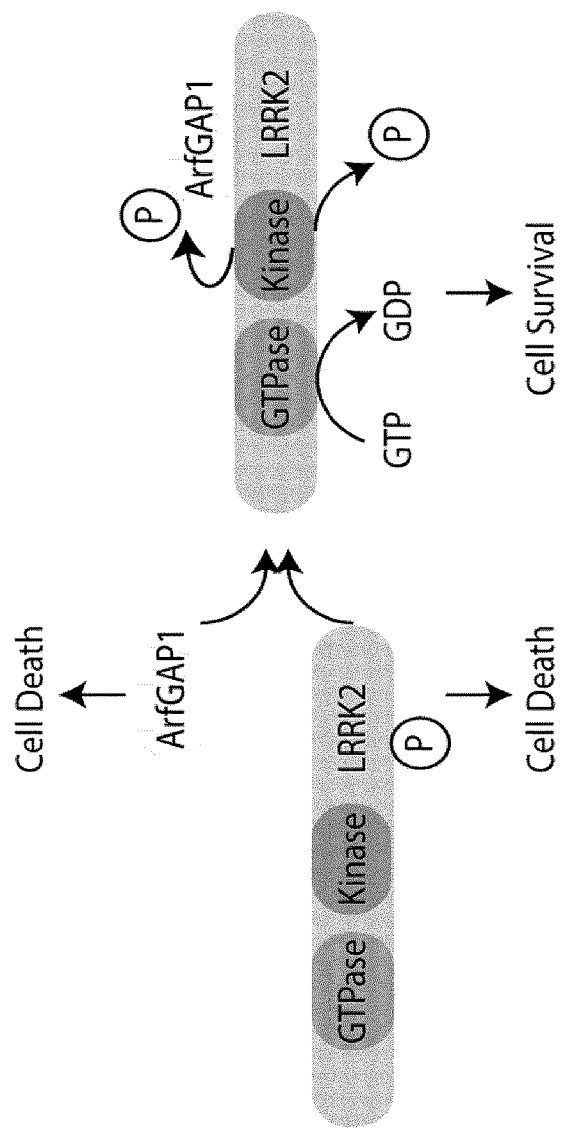
FIG. 3 illustrates the model of reciprocal regulation between ArfGAP1 and LRRK2. Increased expression of LRRK2, or mutations that increase LRRK2 kinase activity, induce cell death. ArfGAP1 binds to LRRK2, promoting hydrolysis of GTP to GDP and decreasing the kinase activity and autophosphorylation of LRRK2. LRRK2 also phosphorylates ArfGAP1, inhibiting its GAP activity. This reciprocal regulation leads to complex effects on cellular viability.

1. The day before screening, the control strain containing the empty plasmid and the selected test strain bearing the plasmid with the gene of interest were inoculated into 2 mL of SC selection medium containing 2% glucose. Cells were grown overnight at 30° C. with shaking at 220 rpm. Note: it can be observed that the yeast strain expressing human expression vector and the yeast strain containing the empty vector grow at the same rate in glucose, which represses ArfGAP1 expression. However, in galactose, where ArfGAP1 expression is stimulated, the yeast strain expressing human ArfGAP1 indeed displays reduced growth relative to yeast grown with empty vector (FIG. 2).

2. The next day, 1 mL of overnight culture was transferred to a microfuge tube and centrifuged at 4700×g for 5 min. The supernatant was discarded, and the pellet was washed with sterile water and centrifuged at 4700×g for 5 min to eliminate traces of glucose.

3. The plates containing the small molecules to be screened was removed from the freezer and thawed at room temperature for approximately 30-60 min.

4. The pellet was suspended in 1-mL sterile water and the A 600 was measured. Cell were diluted to A 600=0.01 in appropriate SC liquid selection medium containing 2% galactose. ≥10 mL of diluted test cells were prepared for each 96-well plate to be tested. A lower volume of control cells was required.

5. 100 μL of test cells was transferred to all but four wells of the sterile 96-well plates using a dispensing eight-channel pipettor. 100-μL medium without yeast was added to two control wells and 100-μL medium with control cells was added to two wells.

6. A control 96-well plate was prepared. To columns 1-4 (32 wells), 100-μL control cells diluted to A 600=0.008 was added. To columns 5-8, 100 μL test cells diluted to A 600=0.01 was added, and to columns 9-12, 100-μL medium without cells was added.

7. The chemicals (small molecule library) were transferred from the storage plates to plates containing yeast using a hand-held pinning tool or a robotic pinning tool. The pinning tool was cleaned and disinfected by dipping and shaking the pins in 10% bleach for 10 s, followed by dipping and shaking in 70% ethanol for 10 s, followed by air drying or drying over a flame. When the pins were cool, the pinning tool was dipped into the chemical storage plate, the pinning tool was then removed carefully without touching the edges of the well and dipped into the test plates without touching the edges of the wells. The pins were removed in the same manner. The pins were washed and disinfected and the process was repeated until all the chemicals had been transferred to the test plates.

8. The plates were placed in the humidifier box and incubated at 30° C. for 40-42 h.

9. Stacks of five plates were shaken on a vortexer at low speed (e.g., setting 4 of a Genie 2 Vortex mixer) for 90 s to resuspend the yeast cells, and the A 600 was measured using a 96-well plate reader.

Growth Restoration Calculation

1. Control plate: The average A 600 of test wells (columns 1-4), control wells (columns 5-8), and medium-only wells (columns 9-12) was calculated.

Figure 4:
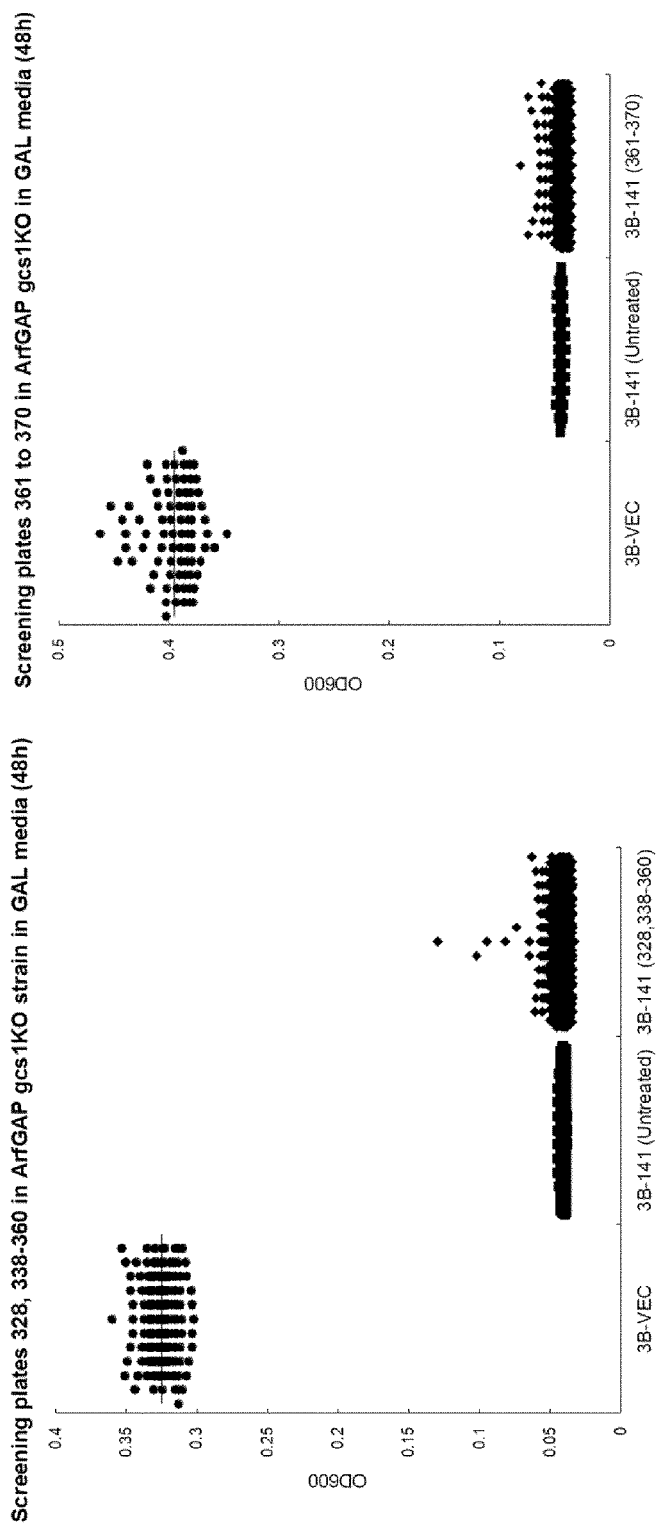
FIG. 4 illustrates the results of screening 33,000 small molecule compounds against yeast gcs1 knockout strains bearing empty vector (3B-VEC) or yeast strains bearing ArfGAP1 expression vectors (3B-141).

2. The A 600 of treated control and human ArfGAP1 expressing yeast strains was plotted. See FIG. 4. The % growth restoration for each compound tested was calculated using the formula: % Growth restoration=(Test & chem−Test)/(Control−Test)×100, where "Test & chem" is the A 600 reading of a well containing the test strain treated with a chemical, "Test" is the average A 600 of test cells not treated with chemicals determined from the control plate, and "Control" is the average A 600 of control cells determined from the control plate.

3. The wells showing highest levels of growth restoration were selected as "actives". Active chemicals for secondary assays were selected if they were obvious outliers and/or showed >50% growth restoration.

Active Chemical Confirmation

1. "Active" wells were visually inspected in an inverted microscope to ensure that the increased A 600 reading was indeed due to an increased number of yeast cells rather than being due to compound precipitation or contamination by other microorganisms.

Figure 5:
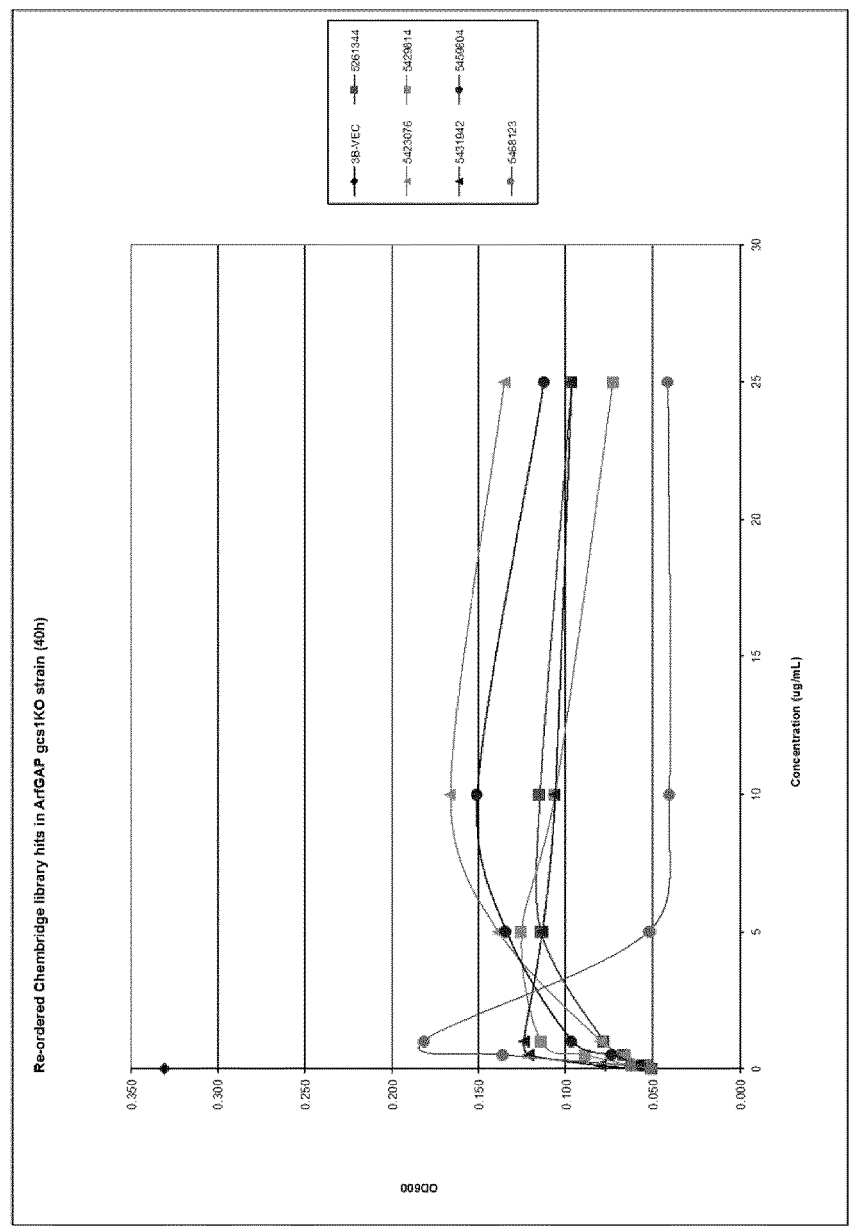
FIG. 5 illustrates the dose-dependent growth of yeast ArfGAP1 gcs1 knockout strains with six small molecules identified from the screen: chembridge ID no.'s 5420376, 5431942, 5468123, 5261344, 5429814, 5459804. The 3B-VEC point represents the growth level of gcs1 knockout yeast strain with empty vector not expressing ArfGAP1.
Figure 6:
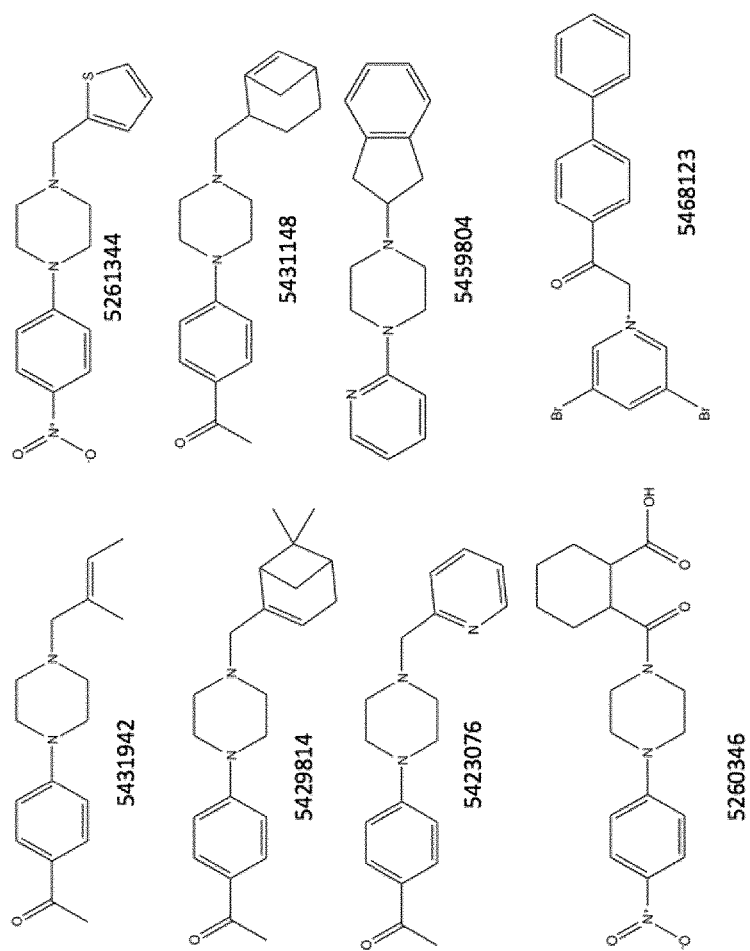
FIG. 6 illustrates the top eight hits from the primary screen in yeast, all of which except 5468123 are phenyl piperazine-derivate molecules

2. To confirm the primary screening results, the activity of each active chemical was retested at various concentrations against both the test and control strains (FIG. 5). The EC 50 for each active compound was established and compounds were selected that combined high potency and low toxicity. Overall, eight compounds were isolated from the screen from among 33,000 small molecules (FIG. 6). Seven of these molecules had a signature phenyl piperazine structure.

3. Note: The active compounds could also be tested against a test strain for an unrelated gene that also causes growth inhibition when overexpressed in yeast. Chemicals that restore growth by general mechanisms, such as interference with the activity of the GAL1 promoter, should also restore growth inhibited by any gene.

The invention claimed is:

1. A method of treating Parkinson's disease in a human subject in need thereof, comprising administering to the subject a compound having the formula:

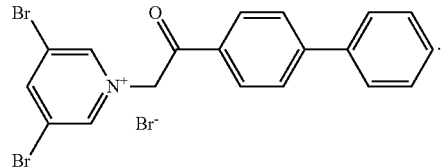 [SMILES: O=C(C[n+]1cc(Br)cc(Br)c1)c1ccc(-c2ccccc2)cc1 ; [Br-]]

2. The method of claim 1, wherein the subject has LRRK2-mutation-induced Parkinson's Disease.

3. The method of claim 2, wherein a genome of the subject carries an autosomal dominant mutation of a LRRK2 gene.

4. A method of treating Parkinson's Disease in a human subject in need thereof, comprising administering to the subject a composition comprising a pharmaceutically acceptable carrier and a therapeutically effective amount of a compound having the formula:

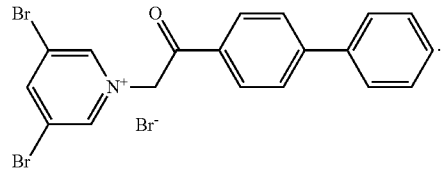 [SMILES: O=C(C[n+]1cc(Br)cc(Br)c1)c1ccc(-c2ccccc2)cc1 ; [Br-]]

5. The method of claim 4, wherein the subject has LRRK2-induced Parkinson's Disease.

6. The method of claim 5, wherein a genome of the subject carries an autosomal dominant mutation of a LRRK2 gene.

* * * * *